(12) United States Patent
Dil Nahlieli

(10) Patent No.: US 11,694,810 B2
(45) Date of Patent: Jul. 4, 2023

(54) SYSTEMS AND METHODS FOR COMPUTING RISK OF PREDICTED MEDICAL OUTCOMES IN PATIENTS TREATED WITH MULTIPLE MEDICATIONS

(71) Applicant: MDI Health Technologies Ltd, Shoham (IL)

(72) Inventor: Dorit Dil Nahlieli, Shoham (IL)

(73) Assignee: MDI Health Technologies Ltd, Shoham (IL)

( * ) Notice: Subject to any disclaimer, the term of this patent is extended or adjusted under 35 U.S.C. 154(b) by 214 days.

(21) Appl. No.: 16/788,336

(22) Filed: Feb. 12, 2020

(65) Prior Publication Data

US 2021/0249137 A1  Aug. 12, 2021

(51) Int. Cl.
G16H 50/30 (2018.01)
G16H 10/60 (2018.01)
G16H 70/40 (2018.01)

(52) U.S. Cl.
CPC ............ G16H 50/30 (2018.01); G16H 10/60 (2018.01); G16H 70/40 (2018.01)

(58) Field of Classification Search
CPC ......... G16H 50/30; G16H 10/60; G16H 70/40
See application file for complete search history.

(56) References Cited

U.S. PATENT DOCUMENTS

| 8,392,220 | B2 | 3/2013 | Knowlton et al. | |
| 8,719,051 | B2 * | 5/2014 | Trifunov | G16H 40/20 |
| | | | | 705/2 |
| 2002/0099273 | A1 * | 7/2002 | Bocionek | G16H 40/63 |
| | | | | 600/300 |
| 2006/0173663 | A1 * | 8/2006 | Langheier | G16H 50/50 |
| | | | | 703/11 |
| 2007/0179806 | A1 | 8/2007 | Knowlton et al. | |

(Continued)

FOREIGN PATENT DOCUMENTS

| CA | 2352629 | | 4/2002 | |
| WO | WO-2019089725 | A1 * | 5/2019 | ............ G16H 20/10 |

*Primary Examiner* — Shahid Merchant
*Assistant Examiner* — Steven G. S. Sanghera

(57) ABSTRACT

There is provided a method comprising: mapping patient-specific medications (mapped to active ingredients) and patient-specific parameters of a patient to a mapping data-structure that maps between medications, predicted medical outcomes, and patient parameters, each relationship-mapping includes one medication (active ingredient), one predicted medical outcome, one patient parameter, one risk score, a predicted medical outcome(s) denoting a medication induced event of a corresponding mapped medication, the patient parameter(s) including: a medication influencing factor (for an active ingredient, selected from primary parameters affecting the corresponding mapped medication: blood level, absorption, distribution, metabolism, elimination) directly affecting the corresponding mapped medication which affects the medication induced event, and/or an event influencing factor directly affecting the medication induced event, and computing an aggregated risk score for each respective predicted medical outcome by aggregating the risk scores of the identified relationship-mappings including each respective predicted medical outcome.

29 Claims, 5 Drawing Sheets

(56) References Cited

U.S. PATENT DOCUMENTS

| | | | |
|---|---|---|---|
| 2014/0350957 A1* | 11/2014 | Calo | G16H 10/60 |
| | | | 705/2 |
| 2015/0178465 A1 | 6/2015 | Knowlton | |
| 2016/0106339 A1* | 4/2016 | Behzadi | A61B 5/6861 |
| | | | 600/302 |
| 2017/0316175 A1* | 11/2017 | Hu | G06N 5/022 |
| 2018/0330824 A1* | 11/2018 | Athey | G16B 20/00 |
| 2019/0228865 A1* | 7/2019 | Dey | G16H 20/10 |
| 2019/0279775 A1* | 9/2019 | Dey | G16H 50/70 |
| 2019/0286936 A1* | 9/2019 | Fuchs | G06K 9/6267 |
| 2020/0074313 A1* | 3/2020 | Sharifi Sedeh | G16H 50/20 |
| 2020/0312434 A1* | 10/2020 | Turgeon | G16H 10/60 |
| 2020/0395129 A1* | 12/2020 | Kalkstein | G16H 50/20 |
| 2021/0202064 A1* | 7/2021 | Neumann | G06N 20/00 |
| 2022/0136971 A1* | 5/2022 | Bauer | G01N 21/35 |
| | | | 356/301 |

\* cited by examiner

SYSTEMS AND METHODS FOR COMPUTING RISK OF PREDICTED MEDICAL OUTCOMES IN PATIENTS TREATED WITH MULTIPLE MEDICATIONS

FIELD AND BACKGROUND OF THE INVENTION

The present invention, in some embodiments thereof, relates to polypharmacy and, more specifically, but not exclusively, to systems and methods for predicting risk of medical outcomes for patients being treated with multiple medications.

An increasingly significant number of patients are being treated with multiple medications, which increases the risk of side effects occurring from interactions between the drugs. For example, patients suffering from cardiovascular disorders may be treated with multiple medications, for blood pressure, cholesterol and/or lipids, and with an anti-coagulant. Such patients may suffer from additional medical conditions, requiring additional treatment, such as diabetes, psychiatric disorders, and sleep disorders. The prescribed medical treatment cocktail may increase the risk of adverse events that may be life threatening.

SUMMARY OF THE INVENTION

According to a first aspect, a computer implemented method of assessing risk of at least one predicted medical outcome for a patient having a plurality of patient-specific parameters and future planned treatment with a plurality of patient-specific medications, for treating the patient, comprises: receiving an indication signal denoting the plurality of patient-specific medications and the plurality of patient-specific parameters, identifying a plurality of relationship-mappings by mapping the plurality of patient-specific medications and the plurality of patient-specific parameters to a mapping data-structure that maps between a plurality of medications, a plurality of predicted medical outcomes, and a plurality of patient parameters, wherein each relationship-mapping includes one respective medication of the plurality of medications, one respective predicted medical outcome of the plurality of medical outcomes, one respective patient parameter of the plurality of patient parameters, and a one respective risk score, wherein at least one of the plurality of relationship-mappings includes a predicted medical outcome denoting a medication induced event of a corresponding mapped medication, and at least one patient parameter selected from the group consisting of: a medication influencing factor directly affecting the corresponding mapped medication which affects the medication induced event, and an event influencing factor directly affecting the medication induced event, wherein the medication influencing factor is selected from the group consisting of the following primary parameters affecting the corresponding mapped medication: blood level, absorption, distribution, metabolism, elimination, wherein at least one patient-specific medication is mapped to a plurality of active ingredients, and wherein a subset of the plurality of relationship-mappings each include a respective active ingredient of the plurality of active ingredients, and the medication influencing factor is for the respective active ingredient, computing an aggregated risk score for each respective predicted medical outcome by aggregating the risk scores of the identified plurality of relationship-mappings including each respective predicted medical outcome, and treating the patient in view of the aggregated risk score for each unique predicted medical outcome.

According to a second aspect, a system for assessing risk of at least one predicted medical outcome for a patient having a plurality of patient-specific parameters and future planned treatment with a plurality of patient-specific medications, for treating the patient, comprises: at least one hardware processor executing a code for: receiving an indication signal denoting the plurality of patient-specific medications and the plurality of patient-specific parameters, identifying a plurality of relationship-mappings by mapping the plurality of patient-specific medications and the plurality of patient-specific parameters to a mapping data-structure that maps between a plurality of medications, a plurality of predicted medical outcomes, and a plurality of patient parameters, wherein each relationship-mapping includes one respective medication of the plurality of medications, one respective predicted medical outcome of the plurality of medical outcomes, one respective patient parameter of the plurality of patient parameters, and a one respective risk score, wherein at least one of the plurality of relationship-mappings includes a predicted medical outcome denoting a medication induced event of a corresponding mapped medication, and at least one patient parameter selected from the group consisting of: a medication influencing factor directly affecting the corresponding mapped medication which affects the medication induced event, and an event influencing factor directly affecting the medication induced event, wherein the medication influencing factor is selected from the group consisting of the following primary parameters affecting the corresponding mapped medication: blood level, absorption, distribution, metabolism, elimination, wherein at least one patient-specific medication is mapped to a plurality of active ingredients, and wherein a subset of the plurality of relationship-mappings each include a respective active ingredient of the plurality of active ingredients, and the medication influencing factor is for the respective active ingredient, computing an aggregated risk score for each respective predicted medical outcome by aggregating the risk scores of the identified plurality of relationship-mappings including each respective predicted medical outcome, and wherein the patient is treated in view of the aggregated risk score for each unique predicted medical outcome.

According to a third aspect, a computer program product for assessing risk of at least one predicted medical outcome for a patient having a plurality of patient-specific parameters and future planned treatment with a plurality of patient-specific medications, for treating the patient, comprising: a non-transitory memory storing thereon code for execution by at least one hardware process, the code including instructions for: receiving an indication signal denoting the plurality of patient-specific medications and the plurality of patient-specific parameters, identifying a plurality of relationship-mappings by mapping the plurality of patient-specific medications and the plurality of patient-specific parameters to a mapping data-structure that maps between a plurality of medications, a plurality of predicted medical outcomes, and a plurality of patient parameters, wherein each relationship-mapping includes one respective medication of the plurality of medications, one respective predicted medical outcome of the plurality of medical outcomes, one respective patient parameter of the plurality of patient parameters, and a one respective risk score, wherein at least one of the plurality of relationship-mappings includes a predicted medical outcome denoting a medication induced event of a corresponding mapped medication, and at least one patient parameter selected from the group consisting of: a medication influencing factor directly affecting the corresponding mapped medication which affects the medication induced event, and an event influencing factor directly affecting the medication induced event, wherein the medication influencing factor is selected from the group consisting of the following primary parameters affecting the corresponding mapped medication: blood level, absorption, distribution, metabolism, elimination, wherein at least one patient-specific medication is mapped to a plurality of active ingredients, and wherein a subset of the plurality of relationship-mappings each include a respective active ingredient of the plurality of active ingredients, and the medication influencing factor is for the respective active ingredient, computing an aggregated risk score for each respective predicted medical outcome by aggregating the risk scores of the identified plurality of relationship-mappings including each respective predicted medical outcome, and wherein the patient is treated in view of the aggregated risk score for each unique predicted medical outcome.

In a further implementation form of the first, second, and third aspects, the medication influencing factor is selected from the group consisting of the following secondary parameters affecting the primary parameter: other medication, medication condition, and non-genetic parameters of the patient that are unrelated to known genetic sequences.

In a further implementation form of the first, second, and third aspects, each aggregated risk score denotes a personalized predicted risk assessment of the patient being treated with the plurality of patient-specific medications and having the patient-specific parameters developing the respective predicted medical outcome, and each respective risk score of each respective relationship-mapping is indicative of a probability of a certain patient being treated with the one respective medication and having the one respective patient parameter, developing the one respective predicted medical outcome.

In a further implementation form of the first, second, and third aspects, the identified plurality of relationship-mappings are clustered according to respective predicted medical outcomes, wherein relationship-mapping members of each cluster have a common predicted medical outcome, and wherein the computing the aggregated risk score comprises aggregating the risk scores of the relationship-mapping members of each respective cluster.

In a further implementation form of the first, second, and third aspects, at least one of the plurality of patient-specific parameters comprises an influence of a certain patient-specific medication on another certain patient-specific medication, and the predicted medical outcome is a result of the influence.

In a further implementation form of the first, second, and third aspects, the aggregated risk score for each respective predicted medical outcome is computed by multiplication of individual risk scores of the identified plurality of relationship-mapping including the respective predicted medical outcome.

In a further implementation form of the first, second, and third aspects, the aggregated risk score denotes a positive increase or a negative decrease relative to a baseline risk score of the respective predicted medication outcome.

In a further implementation form of the first, second, and third aspects, further comprising receiving an indication signal denoting an adjustment of at least one of the plurality of patient-specific medications, wherein the adjustment is selected from the group consisting of: removal, replacement, adjustment of dose, and addition, and iterating using the adjustment of the at least one of the plurality of patient-specific medications, the identifying the plurality of relationship-mappings, the computing the aggregated risk factor, for treatment of the patient.

In a further implementation form of the first, second, and third aspects, the adjustment is iterated until the aggregated risk score for each respective predicted medical outcome is less than a risk threshold, and instructions are generated for treating the patient to prevent or reduce risk of each respective predicted medical outcome below the risk threshold.

In a further implementation form of the first, second, and third aspects, further comprising receiving an indication signal denoting an adjustment of at least one of the plurality of patient-specific parameters, wherein the adjustment is selected from the group consisting of: removal, replacement, adjustment of value, and addition, and iterating using the adjustment of the at least one of the plurality of patient-specific parameters, the identifying the plurality of relationship-mappings, the computing the aggregated risk factor, and instructions are generated for treatment of the patient using the adjustment.

In a further implementation form of the first, second, and third aspects, the adjustment is iterated until the aggregated risk score for each respective predicted medical outcome is less than a risk threshold, and the instructions are generated for treating the patient to prevent or reduce risk of each respective predicted medical outcome below the risk threshold.

In a further implementation form of the first, second, and third aspects, further comprising creating and/or updating the mapping data-structure, by: obtaining raw medical data, extracting a plurality of features from the raw medical data corresponding to at least one medication, at least one predicted medical outcome, at least one patient parameter, and values for computing a corresponding risk value, computing at least one relationship-mapping between the extracted features, and storing the at least one relationship-mapping in the mapping data-structure.

In a further implementation form of the first, second, and third aspects, the raw medical data is extracted using natural language processing (NLP) from one or more members of the group consisting of: formal prescribing information, pharmaceutical leaflets, drug information databases, medical database, medical literature, clinical trials, adverse drug reaction reports.

In a further implementation form of the first, second, and third aspects, computing the aggregated risk score comprises determining a risk classification category of a plurality of risk classification categories each indicative of a range of values of risk scores.

In a further implementation form of the first, second, and third aspects, further comprising generating instructions for presenting a table of risk classification categories, and placing each respective predicted medical outcome into one of the risk classification categories of the table according to the respective determined risk classification category.

In a further implementation form of the first, second, and third aspects, each predicted medical outcome stored in the mapping data-structure is associated with a certain severity category selected from a plurality of severity categories, and the presented table includes a plurality of cells each denoting a respective risk classification category and a respective severity category, wherein each respective predicted medical outcome is placed into one of the plurality of cells based on the corresponding aggregated risk score and corresponding certain severity category.

In a further implementation form of the first, second, and third aspects, when at least one of the plurality of patient-specific parameters matches at least one predicted medical outcome, creating a set of cells in the table denoting current medical outcomes, and placing each of the plurality of patient-specific parameters into one of the cells according to respective severity category of the respective current medical outcome.

In a further implementation form of the first, second, and third aspects, the plurality of patient-specific parameters are non-genetic parameters that are unrelated to known genetic sequences.

In a further implementation form of the first, second, and third aspects, the non-genetic patient-specific parameters of the patient are selected from the group consisting of: smoking, alcohol, nutrition, amount of exercise, occupation, lifestyle data, past usage of medications, current usage of medications, current medical conditions, past medical condition, past medical treatments, current diagnosis, symptoms, lab test results, and imaging results.

In a further implementation form of the first, second, and third aspects, further comprising, analyzing for each respective predicted medical outcome, the identified plurality of relationship-mappings including the respective predicted medical outcome to determine at least one medication and/or at least one patient parameter contributing statistically significantly and disproportionately to the computed aggregated risk score relative to other medications and/or other patient parameters, and providing the determined at least one medication and/or at least one patient parameter as a significant risk factor for the patient for developing the respective medical outcome, and further comprising selecting an adjustment for the at least one medication and/or at least one patient parameter for reducing risk of the respective medical outcome to below a risk threshold, and instructions are generated for treatment of the patient based on the selected adjustment.

In a further implementation form of the first, second, and third aspects, further comprising generating a training dataset, by obtaining a respective plurality of patient-specific medications and patient-specific parameters for each of a plurality of sample patients denoting an input vector, and computing the corresponding aggregated risk score for each respective predicted medical outcome for each of the plurality of sample patients denoting an output vector, wherein the training dataset is for training a machine learning model for prediction of an aggregated risk score for each respective predicted medical outcome in response to being fed a plurality of patient-specific medications and a plurality of patient-specific parameters for a target patient.

In a further implementation form of the first, second, and third aspects, further comprising generating instructions for generating a plurality of dynamic drug labels, each dynamic drug label computed for each one of the plurality of patient-specific medications, each dynamic drug label including a plurality of sub-aggregated risk scores, each sub-aggregated risk score computed for each respective predicted medical outcome of the respective patient-specific medication by aggregating the risk scores of the identified plurality of relationship-mappings including the respective predicted medical outcome and the respective patient-specific medication.

In a further implementation form of the first, second, and third aspects, further comprising dynamically updating each one of the plurality of dynamic labels based on an update of the mapping data-structure.

In a further implementation form of the first, second, and third aspects, wherein at least one of the plurality of predicted medical outcomes denote an efficacy of treating a target disease, and the aggregated risk score for the at least one of the plurality of predicted medical outcomes comprises a change in efficacy relative to a baseline efficacy.

In a further implementation form of the first, second, and third aspects, further comprising monitoring aggregated risk scores for the predicted medical outcomes, by: computing a plurality of aggregated risk scores for each respective predicted medical outcomes over a plurality of time intervals, computing a trend according to the plurality of aggregated risk scores, and analyzing the trend to generate an alert when at least one of the aggregated risk scores is predicted to cross a threshold.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
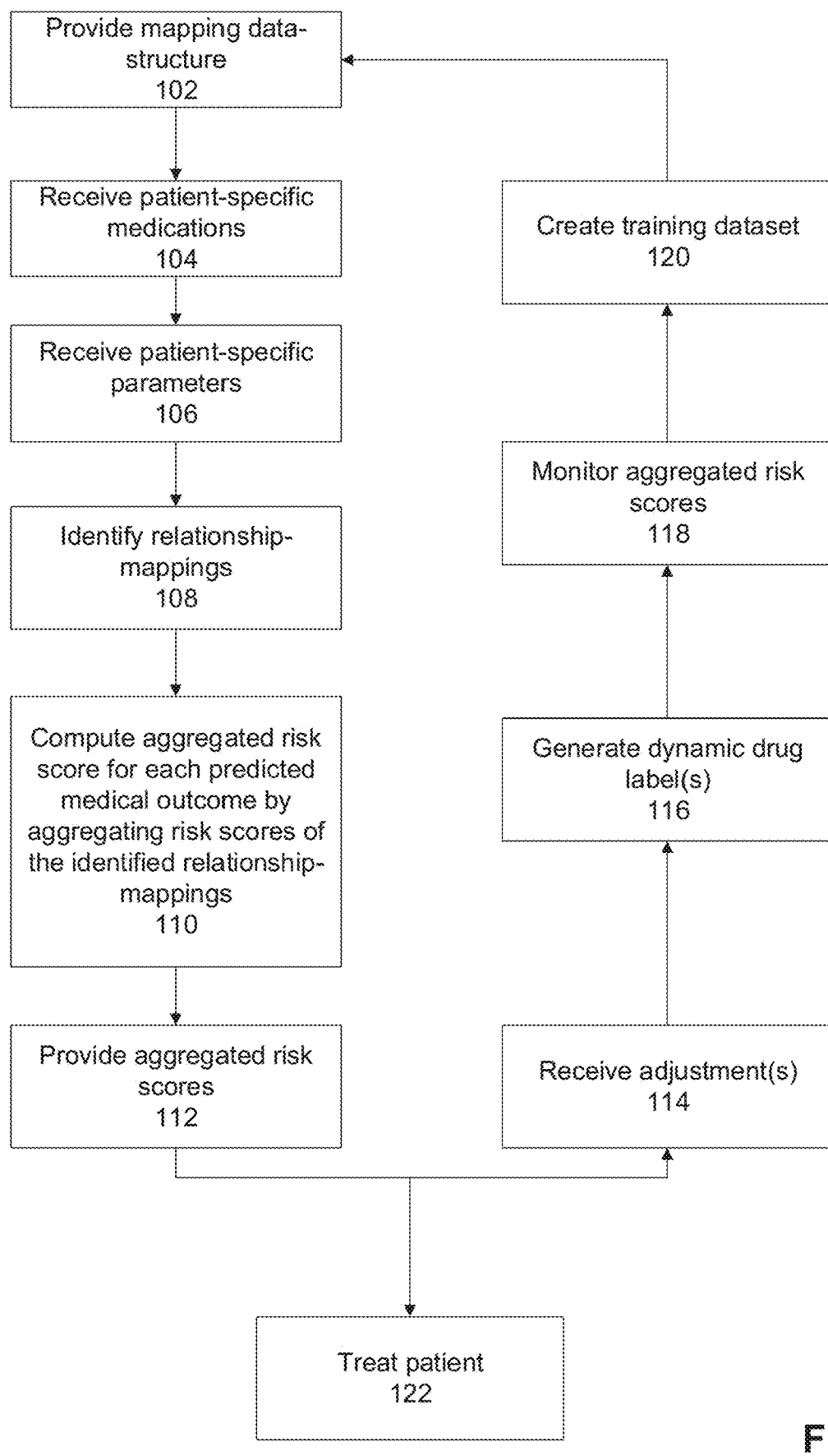
FIG. 1 is a flowchart of a method for computing an aggregated risk for one or more predicted medical outcomes occurring to a patient associated with patient-specific parameters and for which treatment with multiple medications is being planned, in accordance with some embodiments of the present invention.

The present invention, in some embodiments thereof, relates to polypharmacy and, more specifically, but not exclusively, to systems and methods for identifying and predicting risk of medical outcomes for patients being treated with multiple medications.

As used herein, the term medication, pharmaceutical, and drug are sometimes interchanged. The term medications may include drugs made by a pharmaceutical company, and/or natural occurring substances which may be consumed raw and/or further processed (e.g., St John's Wort) that are not necessarily manufactured by a pharmaceutical company, for example, classified as natural remedies and/or nutritional supplements. Exemplary medications include, for example, prescribed pharmaceuticals, over the counter drugs, in hospital medications (e.g., chemotherapy, other anticancer drugs), alternative medicine medications, natural herbs, food additives, and homeopathic medications.

A medication may include: (i) one or more active ingredients with non-active ingredients, or (ii) two or more active ingredients optionally with non-active ingredients. The active ingredients may represent sub-components of the medication. A single medication may be broken down into multiple active ingredients, with each active ingredient being independently evaluated, as described herein. The active ingredients may represent the smallest active component of the medication. The same two or more active ingredients may be combined in different ways to create multiple medications. Multiple different medications may be broken down into active ingredients that are common, for example, medications A and medications B both include active ingredients C and D.

An aspect of some embodiments of the present invention relates to systems, methods, an apparatus, and/or code instructions (e.g., stored on a memory and executable by hardware processor(s)) for assessing predicted risk of medical outcome(s) for a patient for which a future treatment and/or a current treatment with multiple medications (referred to herein as patient-specific medications) is planned and/or currently being administered. Patient-specific parameters that indicate personal data of the patient, are obtained. Relationship-mappings are identified by mapping the patient-specific medications and the patient-specific parameters to a mapping data-structure. The mapping data-structure maps between medications, patient parameters and predicted medical outcomes. Each identified relationship-mapping includes one respective medication, one respective predicted medical outcome, one respective patient parameter, and a respective risk score. The risk score is indicative of a probability of a certain patient developing the respective predicted medical outcome when treated with the respective medication and when the patient has the respective patient parameter. An aggregated risk score is computed for each respective unique predicted medical outcome by aggregating the risk scores of the identified relationship-mappings that include the respective predicted medical outcome. The patient may be treated in view of the aggregated risk score compute for each unique predicted medical outcome.

Optionally, at least one of the identified relationship-mappings includes a predicted medical outcome denoting a medication induced event of a corresponding mapped medication (i.e., of the same identified relationship-mapping), and a patient parameter (i.e., of the same identified relationship-mapping) selected from the group consisting of: a medication influencing factor directly affecting the corresponding mapped medication which affects the medication induced event, and an event influencing factor directly affecting the medication induced event. Optionally, the medication influencing factor is a pharmacodynamics and/or pharmacokinetic parameter, for example, selected from the group consisting of the following primary parameters affecting the corresponding mapped medication (i.e., of the same identified relationship-mapping): absorption, distribution, blood level, metabolism, half life elimination, and excretion. Optionally, the medication influencing factor is one or more of the following secondary parameters affecting the primary parameter: other medication, medical condition (i.e., background and/or current medical conditions, including indication for which the medication is being prescribed), and non-genetic parameters of the patient that are unrelated to known genetic sequences. The medication influencing factor and/or event influencing factor may be considered as patient parameters when such factors are personalized for the certain patient according to how the factors affect medications once consumed by the certain patient. For example, the pharmacodynamics and/or pharmacokinetic parameters effects may be different for different patients and/or for different situations and/or for different medical conditions.

Optionally, one or more (e.g., each) of the patient-specific medications is mapped to multiple active ingredients. Relationship-mappings are identified for each of the active ingredients in the mapping data-structure (e.g., each active ingredient is stored as a patient medication). The medication influencing factor in such a case is for the respective active ingredient. Breaking down the medication into its active ingredients, and aggregating the individual risk scores of the identified relationship-mappings for the active ingredients has been found by Inventors to provide an accurate aggregated risk score for predicted medical outcomes for the patient taking the medications.

As used herein, the term patient-specific medication may sometimes refer to the multiple active ingredients of the patient-specific medication.

The mapping data-structure described herein maps drugs to predicted medical outcomes denoting a medical induced event of a corresponding mapped medication (i.e., of the same relationship-mapping) and/or the event influencing factor related to the medication induced event. Each medication may relate to a different set of events and influencing factors that are based on the unique characteristics of the respective medication. The mapping data-structure maps medications (e.g., each medication) to corresponding medical outcomes (e.g., drug induced events, adverse drug reactions (ADR)) and related influencing factors. The influencing factors contribute to the computation of the aggregated risk score indicative of likelihood of the patient developing an ADR and/or severity of the ADR.

Each medication induced event may be influenced by a variety of factors, including factors that affect the medication directly (and in that way affect the event occurrence) and/or factors that affect the events directly. For example, drug influencing factors may affect the drug's blood level, and may influence absorption, distribution, metabolism and/or elimination (i.e., pharmacokinetic parameters). Drug influencing factors may be other medications that affect the pharmacokinetic parameters, for example, other medication(s) that inhibit the drug's metabolism and/or reduces absorption, and/or a medical condition(s) that affect the drug elimination, such as renal or hepatic impairment. These influencers may be medical conditions, other medications, genetics, lifestyle, and the like. Event influencing factors may be patient-specific parameters that may affect the event's occurrence for the specific patient, for example, medical history, drug history, other medications that affect the event but not the drug. For example, for the medication dabigatran (also known as Pradaxa), every event (e.g., hemorrhagic stroke) has a baseline risk (e.g., obtained from the medical literature) that changes according to the patients-specific parameters that influence the event's risk, for example, other drugs that causes specific events (e.g., GI bleeding), medical history (e.g., bleeding in the past), renal impairment (e.g., that causes higher drug levels) and the like.

Optionally, one or more of the patient-specific parameters and/or one or more of the patient-specific medications are adjusted until the aggregated risk score for each respective predicted medical outcome is below a threshold indicating a tolerated risk level. The patient is instructed to obtain the adjusted patient-specific parameters (e.g., change diet, stop smoking) and/or is treated with the adjusted patient-specific medications, which are predicted to lead to one or more of the predicted medical outcomes at a tolerated risk level (i.e., below the threshold).

At least some of the systems, methods, apparatus, and/or code instructions described herein address the technical problem of treating a patient with multiple medications. Each additional medication prescribed to the patient may increase risk of an adverse side effect, which may result from interactions between two or more of the prescribed medications. However, the additional medications may be needed in order to treat medical conditions of the patient. It is difficult if not impossible for a healthcare provider to adequately obtain a picture of the risks and benefits of the poly-pharmaceutical treatment, and/or how changing one or more of the prescribed drugs affects risk of medical outcome occurring to the patient. Moreover, since each patient may have other risk factors that contribute to the risk of medical outcomes, selecting a suitable multi-medication treatment plan that balances risk and benefit is difficult. Existing tools are inadequate, and/or perform different tasks. For example:

Existing approaches compute interactions only between two medications, which are not applicable to patients being treated with three or more medications. In contrast, at least some of the systems, methods, apparatus, and/or code instructions described herein compute interactions for three or more medications. Moreover, the computational cost (e.g., amount of memory, processor utilization, processing time) increases approximately linearly for increasing number of medications, which improves performance of the computing device computing the risk score. Risk for patients taking a large number of medications (e.g., 7-10 or other values) may be quickly evaluated.

Existing approaches compute interactions between medications without consideration of effects of patient-specific parameters. The general results are provided for any patient and do not reflect differences between patients. In contrast, at least some of the systems, methods, apparatus, and/or code instructions described herein compute interactions based on patient-specific parameters, which may lead to different risk scores for different patients in developing the same (or different) medical outcomes.

Existing approaches consider the medication, without considering the entire detailed and specified effects of individual active ingredients and/or without considering parameters specific to the target patient. In contrast, at least some of the systems, methods, apparatus, and/or code instructions described herein consider one or multiple active ingredients of the medication and their detailed and specified effects (e.g., pharmacokinetics and/or pharmacodynamics) and/or effects of the active ingredients within the target patient and/or parameters specific to the target patient, by computing risk of medical outcome due to interactions and/or influences based on the different individual active ingredients of the drugs and/or their mechanisms of action, and/or considering influence of parameters of the target patient, which may further enable integration of new research on the active ingredients.

Existing approaches consider effects of a single drug (or independently evaluate each drug of a poly-pharmaceutical treatment) on the specific patient, for example, based on the patient's genetic sequences, without considering effects of treatment of multiple medications. In contrast, at least some of the systems, methods, apparatus, and/or code instructions described herein compute risk of predicted medical outcomes due to interactions of multiple drugs in view of patient specific parameters.

At least some of the systems, methods, apparatus, and/or code instructions described herein address the technical problem of predicting risk of medical outcomes (sometimes referred to as adverse drug reactions) in a patient being treated with multiple medications (e.g., over 2, 3, 4, 5, or greater number of medications). Different patients treated with the same combination of medications may experience different risks for developing the same medical outcome, for example, due to the personal factors of each patient (referred to herein as patient-specific parameters). For example, one patient may develop one medical outcome, while another patient develops a different medical outcome. In another example, the risk for one patient developing a certain medical outcome is low, while in another patient the risk of developing the same medical outcome is high. Predicting risk of medical outcome for polypharmacy combinations is challenging due to the large number of possible combinations of drugs, especially when 3, 4, 5, or more drugs are used, since it is clinically impossible to perform clinical trials for all different combinations of drugs. Moreover, since the same medications may affect each patient differently, it is impossible to evaluate different combinations of drugs for all different patient populations and their different medical conditions, medical history and other different personal parameters At least some of the systems, methods, apparatus, and/or code instructions described herein improve the technology of computing a probability or other measure of likelihood of occurrence for predicted medical outcomes or medication related problems in a patient being treated (or for which treatment is being planned) with multiple medications. The improvement includes a customized risk score that takes into consideration patient and medication-specific parameters. Inventors discovered that by mapping the medications into their corresponding active ingredients, and individually considering the effects of the pharmacodynamics and/or pharmacokinetics of the active ingredients, effects of one drug on another drug in a specific patient and/or effects of multiple-medications on a specific patient may be predicted by aggregating the individual results. Moreover, Inventors discovered that an aggregated risk score of predicted medical outcomes may be estimated by considering individual relationship-mappings between one medication, one predicted medical outcome, and one patient parameter, where each relationship-mapping is associated with an individual risk score, by aggregating the individual risk scores. Aggregation of individual risk scores of individual relationship-mappings was discovered by Inventors to provide a good estimate of the aggregated risk score.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
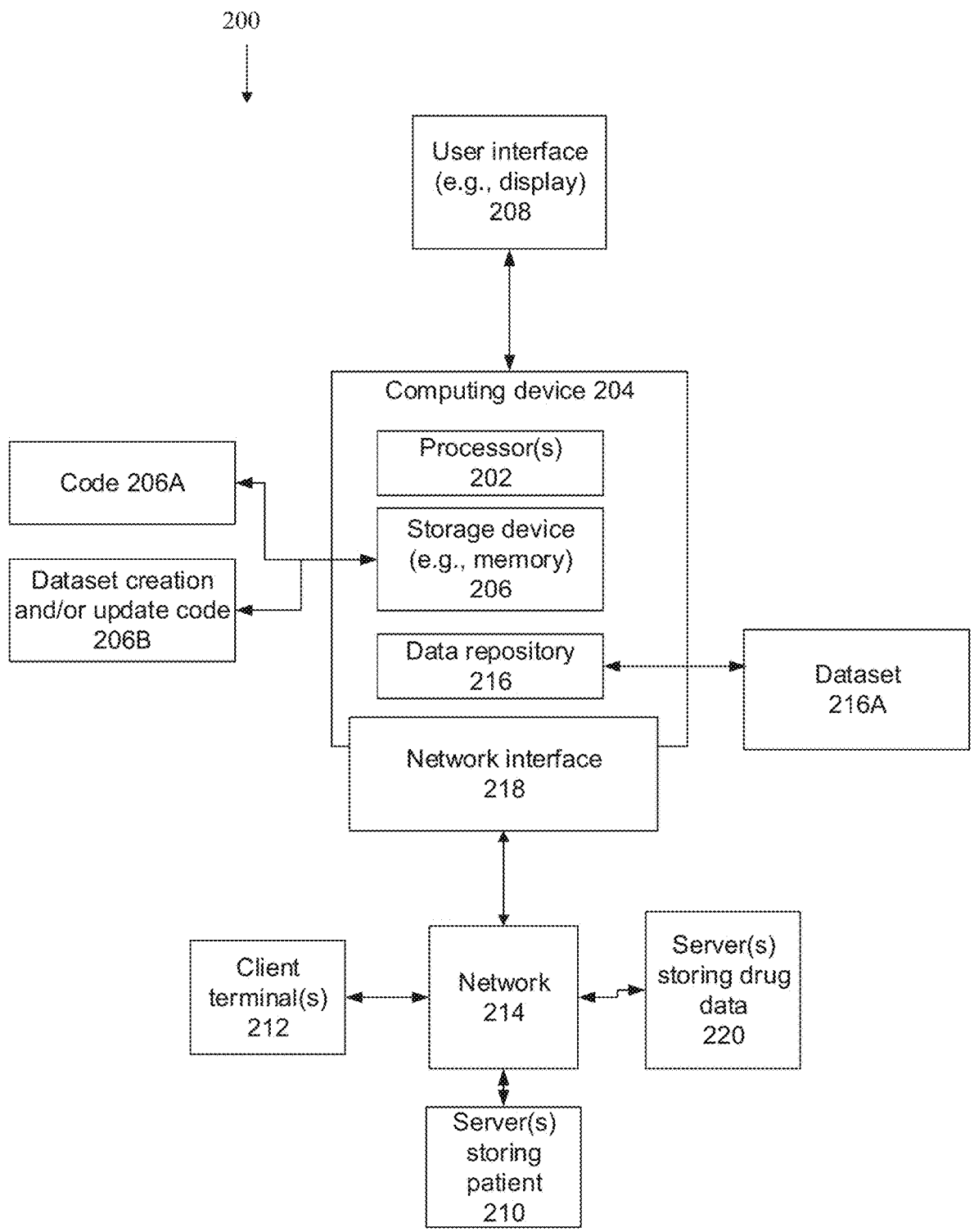
FIG. 2 is a block diagram of a system for computing an aggregated risk for one or more predicted medical outcomes occurring to a patient associated with patient-specific parameters and for which treatment with multiple medications is being planned, in accordance with some embodiments of the present invention.
Figure 3:
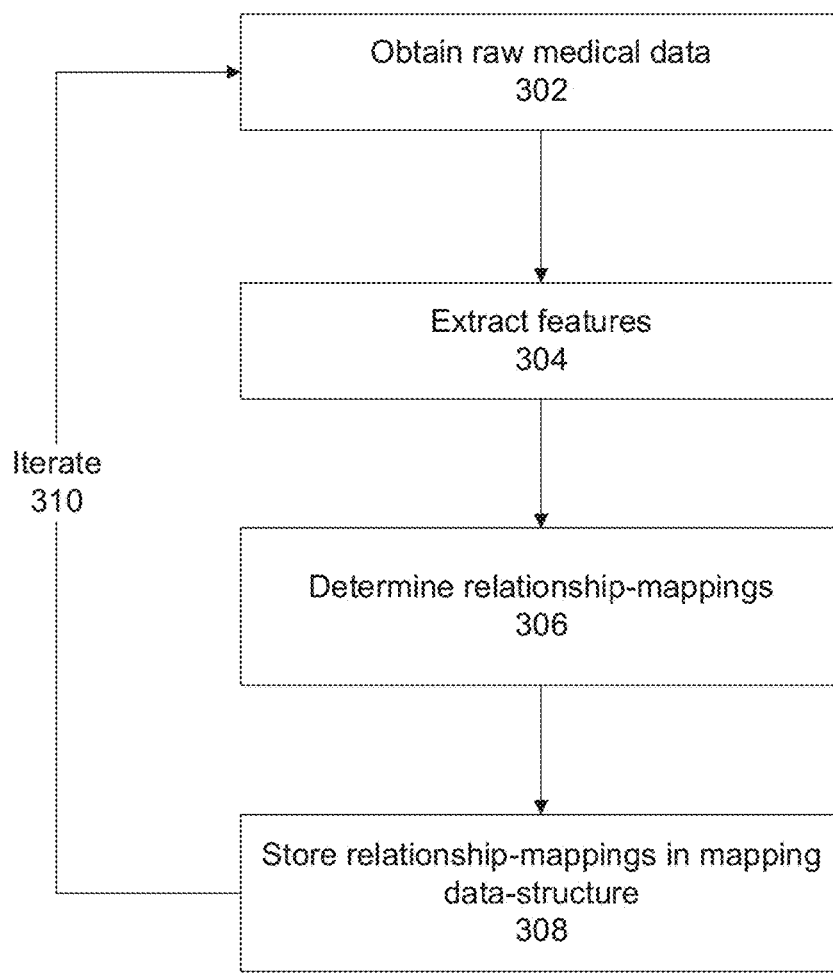
FIG. 3 is a flowchart of an exemplary method for creating and/or updating a mapping data-structure that maps between medications, predicted medical outcomes, and patient parameters, and that includes individual risk scores for individual relationship-mappings, in accordance with some embodiments of the present invention.

Reference is now made to FIG. 1, which is a flowchart of a method for computing an aggregated risk for one or more predicted medical outcomes occurring to a patient associated with patient-specific parameters and for which treatment with multiple medications is being planned, in accordance with some embodiments of the present invention. Reference is also made to FIG. 2, which is a block diagram of a system for computing an aggregated risk for one or more predicted medical outcomes occurring to a patient associated with patient-specific parameters and for which treatment with multiple medications is being planned, in accordance with some embodiments of the present invention. Reference is also made to FIG. 3, which is a flowchart of an exemplary method for creating and/or updating a mapping data-structure that maps between medications, predicted medical outcomes, and patient parameters, and that includes individual risk scores for individual relationship-mappings, in accordance with some embodiments of the present invention.

System 200 may implement the acts of the method described with reference to FIGS. 1 and/or 3 (and/or other Figures described herein), by processor(s) 202 of a computing device 204 executing code instructions 206A and/or 206B stored in a storage device 206 (also referred to as a memory and/or program store).

Computing device 204 may be implemented as, for example, a client terminal, a server, a computing cloud, a virtual server, a virtual machine, a mobile device, a desktop computer, a thin client, a Smartphone, a Tablet computer, a laptop computer, a wearable computer, glasses computer, and a watch computer.

Multiple architectures of system 200 based on computing device 204 may be implemented. In an exemplary implementation, computing device 204 storing code 206A and/or 206B, may be implemented as one or more servers (e.g., network server, web server, a computing cloud, a virtual server) that provides services (e.g., one or more of the acts described with reference to FIG. 1) to one or more client terminals 212 over a network 214, for example, providing software as a service (SaaS) to the client terminal(s) 212, providing software services accessible using a software interface (e.g., application programming interface (API), software development kit (SDK)), providing an application for local download to the client terminal(s) 212, and/or providing functions using a remote access session to the client terminals 212, such as through a web browser. For example, physicians having client terminals 212 installed in their offices (or using mobile devices) use their local client terminals to access computing device 204, which may be remotely located. The physician users may enter the patient-specific parameters and/or patient-specific medications, and computing device 204 computes the aggregated risk of one or more predicted medical outcomes, as described herein. In another example, computing device 204 may include locally stored software (e.g., code 206A and/or 206B) that performs one or more of the acts described with reference to FIG. 1, for example, as a self-contained client terminal. In another example, client terminals 212 may obtain the mapping data-structure 216A from computing device 204 (which may compute and/or update the mapping data-structure 216A using code 206B) for local installation and use. Each client terminal 212 (e.g., of respective medical facilities) may store its own copy of the mapping data-structure 216A, for local computation of aggregated risk score of patients (e.g., patients being treated at the respective medical facility).

Processor(s) 202 of computing device 204 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include a single processor, or multiple processors (homogenous or heterogeneous) arranged for parallel processing, as clusters and/or as one or more multi core processing devices.

Data storage device 206 stores code instructions executable by processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Storage device 206 stores code 206A that implements one or more features and/or acts of the method described with reference to FIG. 1 when executed by processor(s) 202. Storage device 206 may store code for creating and/or updating mapping data-structure 206B, for example, as described with reference to FIG. 3.

Computing device 204 may include a data repository 216 for storing data, for example, mapping data-structure 216A, and/or a machine learning model 216B which may be trained as described herein. Data repository 216 may be implemented as, for example, a memory, a local hard-drive, virtual storage, a removable storage unit, an optical disk, a storage device, and/or as a remote server and/or computing cloud (e.g., accessed using a network connection).

Network 214 may be implemented as, for example, the internet, a local area network, a virtual private network, a wireless network, a cellular network, a local bus, a point to point link (e.g., wired), and/or combinations of the aforementioned.

Computing device 204 may include a network interface 218 for connecting to network 214, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may connect using network 214 (or another communication channel, such as through a direct link (e.g., cable, wireless) and/or indirect link (e.g., via an intermediary computing unit such as a server, and/or via a storage device) with one or more of:

Server(s) storing medication data 220, for obtaining raw data from which medication information, such as data of sub-components of the medication, is extracted and inserted into the mapping data-structure 216A, as described herein.

Server(s) storing patient parameters 210, which include the patient-specific parameters for the current patient, for example, electronic health records, laboratory server, medical imaging server, PACS server, and/or an interface (e.g., graphical user interface (GUI)) into which a user manually enters the patient data.

Client terminal(s) 212, which may be used by users remotely accessing computing device 204, as described herein.

Computing device 204 and/or client terminal(s) 212 include and/or are in communication with one or more physical user interfaces 208 that include a mechanism for a user to enter data (e.g., patient-specific parameters and/or patient-specific medications) and/or view the displayed computed aggregated risk scores, optionally within a GUI. Exemplary user interfaces 208 include, for example, one or more of, a touchscreen, a display, a keyboard, a mouse, and voice activated software using speakers and microphone.

At 102, a mapping data-structure is provided. The mapping data-structure may be created and/or dynamically updated, for example, as described below in additional detail with reference to FIG. 3.

The mapping data-structure maps between medications, predicted medical outcomes, and patient parameters. Each relationship-mapping includes one respective medication, one respective predicted medical outcome, one respective patient parameter, and one respective individual risk score.

The medications stored in the mapping data-structure may include active ingredients of drugs and/or may include the drugs themselves. The drug may be mapped into its active ingredients, for example, by using a look-up table created from a prior analysis of drug literature, and/or accessing a database of medications. When the medications are active ingredients of drugs, the mapping data-structure maps between active ingredients, predicted medical outcomes, and patient parameters, where each relationship-mapping includes one respective active ingredient, one respective predicted medical outcome, one respective patient parameter, and one respective individual risk score. The aggregated risk score is computed using the individual risk scores for the relationship-mappings including the active ingredients of each relevant patient-specific medication, for example, as described below with reference to 110.

It is noted that multiple unique medications may have one or more active ingredients in common, and may map to the same relationship-mapping(s) that includes the common active ingredient(s).

Figure 4:
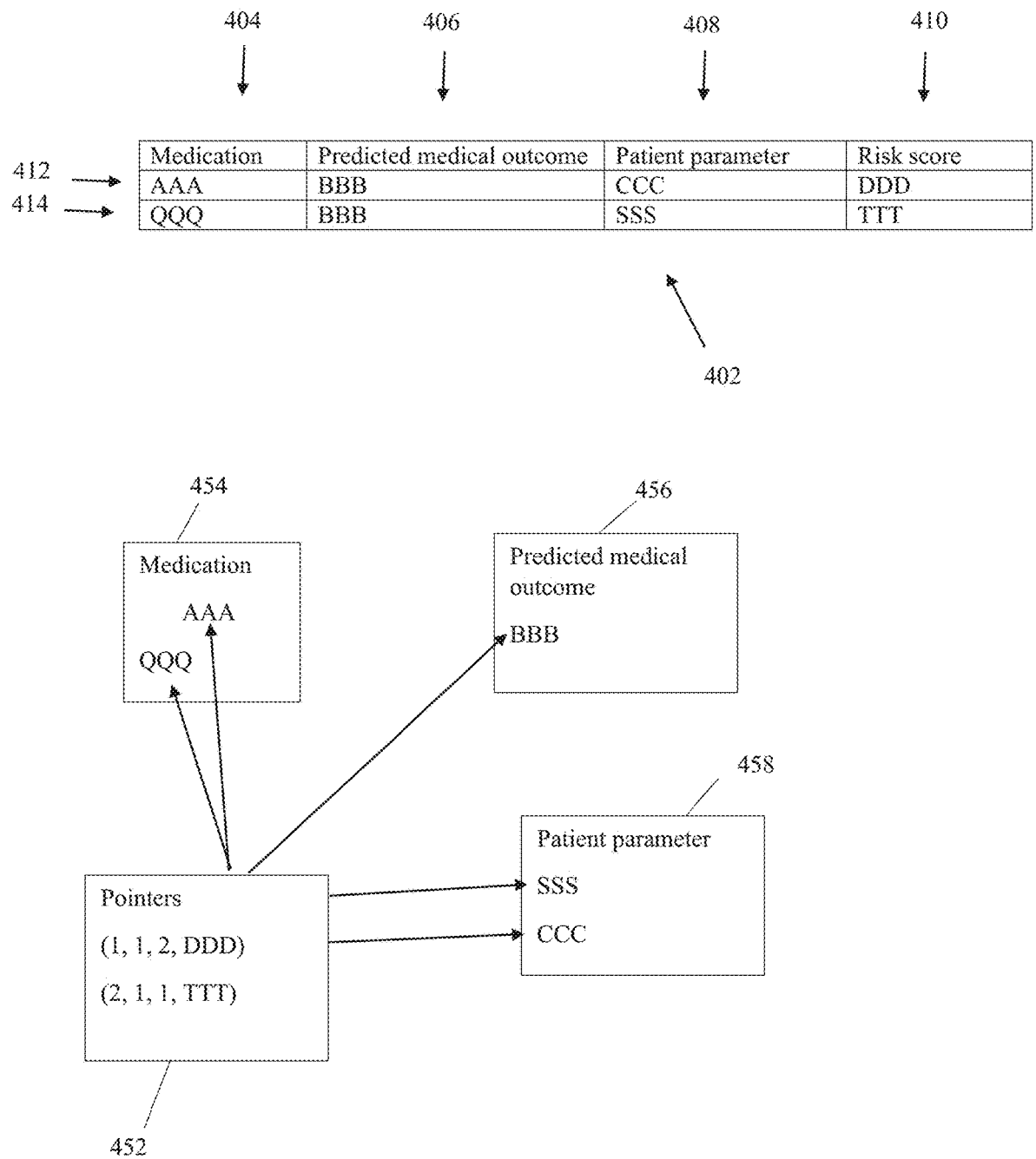
FIG. 4 is a schematic depicting exemplary implementations of the mapping data-structure as a table and/or set of pointers, in accordance with some embodiments of the present invention.

Reference is now made to FIG. 4, which is a schematic depicting exemplary implementations of the mapping data-structure as a table 402 and/or set of pointers 452, in accordance with some embodiments of the present invention.

The mapping data-structure may be implemented, for example, as table 402, where one column is designated for each of: the medications 404, predicted medical outcomes 406, patient parameters 408, and risk score 410, and each row of the table defines one relationship-mapping 412, 414. Each cell of each row for each column (i.e., each relationship-mapping) stores one value for each of the: one respective medication, one respective predicted medical outcome, one respective patient parameter, and one respective risk score. For example, the row 412 storing values AAA, BBB, CCC, DDD, denotes the relationship-mapping of the medication AAA, the medical outcome BBB, and the patient parameter CCC, with risk score DDD. The row 414 storing values QQQ, RRR, SSS, TTT, denotes the relationship-mapping of the medication QQQ, the medical outcome BBB, and the patient parameter SSS, with risk score TTT.

As described herein, when rows 412 and 414 are identified as relevant relationship-mappings, such as by the patient taking patient-specific medications AAA and QQQ, and the patient having patient-specific parameters CCC and SSS, the aggregated risk score for predicted medical outcome BBB is computed based on individual risk scores DDD and TTT.

It is noted that rows 412 and 414 may represent relationship-mappings for the active ingredients of a certain medication, i.e., medications AAA and QQQ in row 404 represent two active ingredients of the certain medication.

In another example, the mapping data-structure may be implemented as a set of pointers 452, triplets, or other suitable data structure, that point between a dataset storing unique predicted medical outcomes 454, a set of unique predicted medical outcomes 456, and a set of unique patient parameters 458. Each set of pointers defines a respective relationship-mapping, and may be associated with the respective risk score for the respective relationship-mapping. For example, the set (1, 1, 2, DDD) stored in pointers 452 denotes the relationship-mapping of the first medication AAA in the medication dataset 454, the first medical outcome BBB of the medical outcome dataset 456, and the second patient parameter CCC in the patient parameter dataset 458, having a risk score of DDD. It is noted that set (1, 1, 2, DDD) of pointers 452 corresponds to the relationship-mapping defined by row 412 of table 402, and set (2, 1, 1, TTT) of pointers 452 corresponds to the relationship-mapping defined by row 414 of table 402.

Referring now back to 102 of FIG. 1, optionally, one or more of the predicted medical outcomes is a value indicative of an efficacy of treating a certain target disease. For the relationship-mapping including the predicted medical outcome indicative of efficacy, the efficacy of treating the target disease is affected by the medication and patient parameter stored in the respective relationship-mapping. Conceptually, how the efficacy of the medication for the patient having the patient parameter is affected in treating the target disease. In such a case, the aggregated risk score computed for the predicted medical outcomes may denote a change in efficacy relative to a baseline efficacy. The efficacy may be an increased effect (i.e., increasing efficacy in treating the medical condition from 50% to 70%) or a decreased effect (i.e., decreased efficacy in treating the medical condition from 50% to 30%).

Optionally, each respective risk score of each respective relationship-mapping (of one respective medication, one respective patient parameter, and one respective predicted medical outcome) is indicative of a probability of a certain patient being treated with the one respective medication and having the one respective patient parameter, developing the one respective predicted medical outcome.

Optionally, at least one of the respective risk scores of a respective relationship-mapping denotes an increase or decrease in risk relative to a baseline. The baseline may be a risk of the certain patient developing a certain predicted medical outcome associated with the relationship-mapping including the respective risk score, without any risk factors. The respective risk score increases or decreases the probability of the certain patient being treated with the one respective medication and having the one respective patient parameter, developing the one respective predicted medical outcome, relative to the baseline of the certain patient developing the one respective predicted medical outcome when not treated with the one respective medication and/or without having the one respective patient parameter.

Exemplary predicted medical outcomes include development of a new medical disease, for example, diabetes, heart disease, autoimmune disease, cancer (optionally of certain types, for example, lymphoma, lung cancer, and skin cancer), a new medical event, experiencing an adverse event, medical symptom, and/or medical sign, for example, internal bleeding, stroke, headache, acute renal failure, lactic acidosis, hepatotoxicity, rhabdomyolysis, intracranial bleeding, Torsades de pointes, agranulocytosis, hyperkalemia, hypokalemia, hypernatremia, hyponatremia, hypertension, hypotension, esophagitis, cognitive decline, falls, gastrointestinal bleeding, central nervous system depression, memory decline, morning sedation, sedation, unsteadiness, myopathy, confusion, fracture, road accident, cancer, traumatic injury, anemia, thrombocytopenia, amnesia, delirium, dementia, depression, respiratory depression, AV block, bradycardia, insomnia, dizziness, drowsiness, constipation, GI symptoms, vomiting, abdominal pain, hyperlipidemia, sexual dysfunction, tachycardia, loss of appetite, B12 deficiency, diarrhea, elevated liver enzymes, hyperglycemia, dyspnea, bronchospasm, fatigue, dehydration, photosensitization, gastritis, cough, nausea, dyspepsia, hematoma, diaphoresis, weight loss, xerostomia, flatulence, diuresis, urinary frequency, heartburn, gynecomastia.

Exemplary predicted medical outcomes include worsening of an existing medical condition, optionally as defined by a certain patient-specific parameter.

Optionally, one or more of the predicted medical outcomes is indicative of a medication induced event of a corresponding mapped medication. Optionally, at least one of the patient parameters is a medication influencing factor directly affecting the corresponding mapped medication which affects the medication induced event. The medication influencing factor may be a primary parameter including pharmacodynamics and/or pharmacokinetic parameter affecting the corresponding mapped medication: blood level, absorption, distribution, metabolism, and elimination. Alternatively or additionally, the medication influencing factor is a secondary parameter that affects the primary parameter, for example: other medication, medication condition, and non-genetic parameters of the patient that are unrelated to known genetic sequences.

Alternatively or additionally, at least one of the patient parameters is an event influencing factor directly affecting the medication induced event, for example, patient-specific parameters that are predicted to affect the event's occurrence for the patient, for example, patient medical history, drug history, and/or other medications the patient is taking that affect the event.

At 104, an indication signal denoting the patient-specific medications for the target patient is received. The medications may be obtained, for example, manually entered by a user (e.g., into a graphical user interface (GUI)), automatically entered by a user (e.g., scanning barcodes of the medications), and/or automatically obtained from a record (e.g., health record of the patient) and/or other data of the patient.

The patient-specific medications may include medications that the patient is being prescribed for future use, i.e., the patient is not currently taking these medications. For example, the user is evaluating the medications that the patient is being prescribed before they are actually prescribed to the patient, to predict future medical outcomes. Alternatively or additionally, the patient-specific medications may include medications that the patient is currently taking. For example, the user is evaluating the currently prescribed medications administered to the patient, to predict future medical outcomes, for example, to consider changes to the medications due to high risk of dangerous predicted events.

At 106, an indication signal denoting the patient-specific parameters for the target patient is received. The parameters may be obtained, for example, manually entered by a user (e.g., into a GUI)), and/or automatically obtained from a record (e.g., health record of the patient) and/or other data of the patient.

The patient-specific parameters may include non-genetic parameters that are unrelated to known genetic sequences, for example, genetic sequences of the patient (e.g., DNA sequences) known to have certain effects, such as effects on efficacy of certain medications, such as increase or decrease in metabolism of certain medications.

Optionally, the patient-specific parameters exclude genetic parameters. Optionally, the patient-specific parameters include only non-genetic parameters. Alternatively, the patient-specific parameters include some genetic parameters and some non-genetic parameters. Alternatively, the patient-specific parameters include only genetic parameters.

Exemplary not necessarily limiting patient-specific parameters of the patient (e.g., non-genetic) include: smoking (i.e., smoker or non-smoker, if smoker pack year history, past smoker), alcohol consumption, nutrition, amount of exercise, occupation, lifestyle data, current diagnosis, symptoms, lab tests results, imaging results, medication history (for example, past usage and effects of medications), current usage of medications, current medical conditions, past medical condition, and past medical treatments.

Optionally, at least one of the patient-specific parameters includes an influence of a certain patient-specific medication on another certain patient-specific medication. In such a case, the predicted medical outcome is a result of the influence. For example, a certain medication (prescribed to the patient) increases efficacy or reduces efficacy of another medication (prescribed to the patient).

The patient-specific parameters and/or the patient-specific medications may be obtained, for example, from the electronic health record (EHR) of the patient, via a GUI designed to help the user manually enter the data, from prescription filling data, laboratory result data, internet of things sensors and/or devices (IOTs), PGx genetic test results, and/or other sources.

At 108, multiple relationship-mappings are identified, by mapping the patient-specific medications and the patient-specific parameters to the mapping data-structure.

Optionally, one or more (e.g., each one) of the patient-specific medications is mapped to a respective set of active ingredients. In such a case, the patient-specific medications relate to the active ingredients of the medication. Each identified relationship-mapping includes one respective active ingredient of one medication.

In an exemplary implementation, all possible combinations of patient-specific medications and patient-specific parameters are determined, and each combination is mapped to one relationship-mapping stored in the mapping data-structure. For example, a row of the mapping data-structure storing the certain combination is identified, and/or a set of pointers mapping between the patient-specific medication and the patient-specific parameters of the certain combination are identified.

The identified relationship-mappings include one or more predicted medical outcomes. The same predicted medical outcome may be included in multiple relationship-mappings for multiple different combinations of patient-specific medications and patient-specific parameters. For example, both the relationship-mapping between patient-specific medication AAA and patient-specific parameter ZZZ, and the relationship-mapping between patient-specific medication BBB and patient-specific parameter YYY, both include predicted medical outcome QQQ.

Optionally, at least one of the identified relationship-mappings includes a predicted medical outcome denoting a medication induced event of a corresponding mapped medication (i.e., of the same identified relationship-mapping), and a patient parameter (i.e., of the same identified relationship-mapping) selected from the group consisting of: a medication influencing factor directly affecting the corresponding mapped medication which affects the medication induced event, and an event influencing factor directly affecting the medication induced event. Optionally, the medication influencing factor is selected from the group consisting of the following primary parameters affecting the corresponding mapped medication (i.e., of the same identified relationship-mapping): blood level, absorption, distribution, metabolism, elimination. Optionally, the medication influencing factor is selected from the group consisting of the following secondary parameters affecting the primary parameter: other medication, medication condition (i.e., disease indication for which the medication is being prescribed), and non-genetic parameters of the patient that are unrelated to known genetic sequences.

At 110, an aggregated risk score is computed for each respective predicted medical outcome by aggregating the risk scores of the identified of relationship-mappings including each respective predicted medical outcome.

Each aggregated risk score denotes a personalized predicted risk assessment of the patient developing the respective predicted medical outcome when being treated with the patient-specific medications and having the patient-specific parameters.

The aggregated risk score may indicate a positive increase or a negative decrease relative to a baseline risk score of the patient respective predicted medical outcome without being treated with the patient-specific medication and/or having the patient-specific parameters of the identified relationship-mappings.

Optionally, an aggregated risk score is computed per unique predicted medical outcome according to the respective risk scores of the relationship-mappings including the respective unique predicted medical outcome. For example, for a first identified relationship-mapping of patient-specific medication AAA, patient-specific parameter ZZZ, predicted medical outcome QQQ, and risk score DDD, and for a second identified relationship-mapping of patient-specific medication BBB, patient-specific parameter YYY, predicted medical outcome QQQ, and risk score EEE, the aggregated risk score is computed for the unique predicted medical outcome QQQ using the risk scores DDD and EEE of the identified two relationship-mappings.

Optionally, aggregated risk score is computed from a clustering of the identified relationship-mappings. The identified relationship-mappings may be clustered according to respective predicted medical outcomes, where relationship-mapping members of each cluster have a common unique predicted medical outcome. The aggregated risk score is computed per cluster, i.e., per unique predicted medical outcome, by aggregating the risk scores of the relationship-mapping members of each respective cluster.

The aggregated risk score for each respective predicted medical outcome may be computed, for example, by multiplication of individual risk scores of the identified relationship-mapping that include the respective predicted medical outcome (e.g., members of each cluster), weighted multiplication of individual risk scores, and/or other function applied to the individual risk scores corresponding to each respective predicted medical outcome.

At 112, the computed aggregated risk score(s) are provided, for example, for further processing, for presentation on a display, for storage in a data storage device, and/or to another computing device (e.g., remote device over a network, and/or locally connected device).

Optionally, the aggregated risk score(s) are further processed.

Optionally, the aggregated risk score is mapped to a risk classification category of multiple candidate risk classification categories, for example, low risk, moderate risk, and high risk. The mapping may be by assigning the value of the aggregated risk score into one of the risk classification categories according to a range of values of risk scores corresponding to each risk classification category, for example, for a risk value between 0-100%, the range 0-25% corresponding to low risk, the range 26-50% corresponding to moderate risk, 51-75% corresponding to high risk, and the range 76-100% corresponding to very high risk.

Optionally, instructions are generated for presenting the aggregated risk score(s), optionally, the risk classification categories(s). The aggregated risk score(s) may be presented as raw numbers. The risk classification categories(s) may be presented as the raw categories, and/or arranged into a table of risk classification categories.

Figure 5:
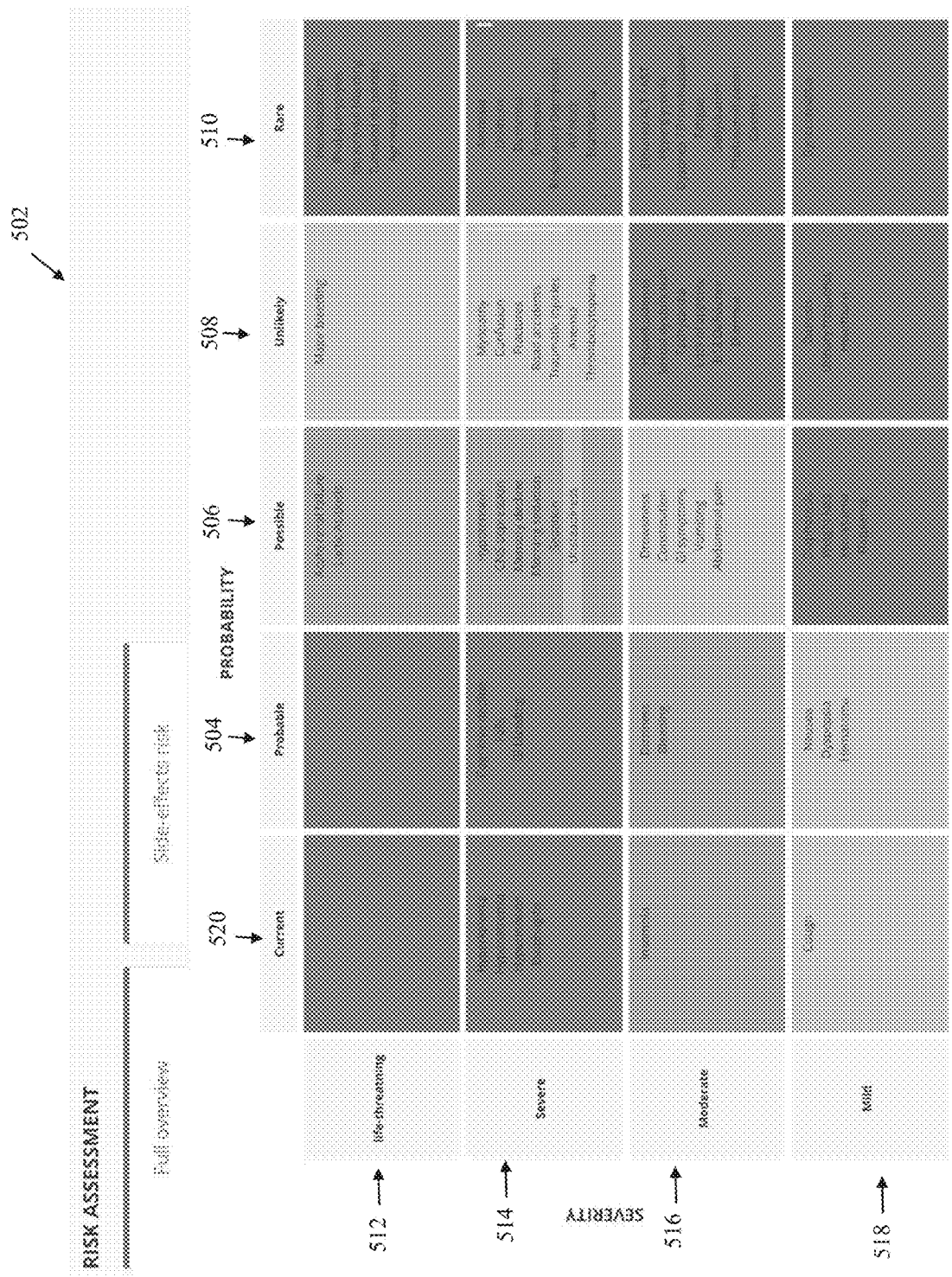
FIG. 5 is a schematic of an exemplary table of risk classification categories, in accordance with some embodiments of the present invention.

Reference is now made to FIG. 5, which is a schematic of an exemplary table 502 of risk classification categories, in accordance with some embodiments of the present invention.

Table 502 may be created by placing each respective predicted medical outcome into one of the risk classification categories of the table according to the respective determined risk classification category corresponding to the computed aggregated risk score, for example, probable 504, possible 506, unlikely 508, and rare 510. Optionally, the cells of the table corresponding to each respective risk category (e.g., columns) are color coded as an indication of the relative risk of the respective risk category. For example, the column of cells corresponding to rare 510 (i.e., very low risk) is colored green, the column of cells corresponding to unlikely 508 (i.e., fairly low risk) is colored yellow, the column of cells corresponding to possible 506 (i.e., moderate risk) is colored orange, and the column of cells corresponding to probably 504 (i.e., high risk) is colored red.

The generated table may include cells each denoting the risk classification categories (e.g., columns) and multiple severity categories (e.g., rows), for example, life threatening 512, severe 514, moderate 516, and mild 518. Optionally, each unique predicted medical outcome stored in the mapping data-structure is associated with a certain severity category selected from the multiple severity categories. Severity categories may be color coded. The assigned severity value may be determined, for example, based on an analysis of current medical literature and/or based on an analysis of medical definitions. For example, major bleeding is determined as being a life-threatening predicted medical outcome, while a cough is determined as being a mild predicted medical outcome. In another example, bleeding may be determined as being moderate when the medical literature indicates that the predicted medical outcome is moderate. Each respective predicted medical outcome is placed into one of the cells based on the corresponding computed aggregated risk score and corresponding severity category.

Optionally, when at least one of the patient-specific parameters matches at least one corresponding predicted medical outcome, denoting that the patient is currently experiencing one of the possible medical outcomes, a set of cells (e.g., column 520) in the table 502 may be created denoting the medical outcomes currently being experienced by the patient. Each of the patient-specific parameters (matching corresponding predicted medical outcome(s)) is placed into one of the cells of the table according to the respective severity category (e.g., 512, 514, 516, 518) of the respective medical outcome currently being experienced by the patient. The generated table provide a visual indication of the severity of the current signs and/or symptoms and/or medical conditions the patient is suffering from.

At 114, indication signals for one or more adjustments are received, and features described with reference to 102 (or 104)-112 may be iterated, for updating and/or re-computing the aggregated risk score. Instructions for treating the patient according to the adjustment may be generated. The patient may be treated according to the adjusted values.

The iterations may be performed by accessing the most updated mapping dataset available, for example, the mapping dataset is dynamically updated in parallel and/or using an independent process, as described with reference to 102.

Adjustments are performed, for example, when the risk of one or more predicted medical outcomes is unacceptable (e.g., risk of internal bleeding being above a threshold). The adjustment may be performed to the prescribed medications. Alternatively or additionally, adjustment(s) is made to the patient-parameters.

Optionally, one or more the patient-specific medications are adjusted. Exemplary adjustments include: removal of an existing medication, replacement of an existing medication with a new medication (e.g., with the help of the indication mapping process described herein), adjustment of dose of one or more medications, and addition of a new medication and/or close monitoring for a specific parameter. The adjustment may be performed in response to a received indication signal, which is generated in response to manual user input (e.g., user changes to one or more medications, for example, by making a new selection using a medication selection user interface (e.g., GUI), and/or in response to automatic input generated by executing code (e.g., process that automatically tries different medications according to a set of rules to obtain a target aggregated risk level below a threshold).

Optionally, the adjustment triggers iteration of 102 (or 104) to 112 until the aggregated risk score for one or more selected (or each one of the) respective predicted medical outcome is less than a target risk threshold. The target risk threshold may be manually and/or automatically set. The patient may be treated (and/or instructions for treating the patient may be generated) using the adjusted value, to prevent or reduce risk of each respective predicted medical outcome below the risk threshold.

Alternatively or additionally, one or more patient-specific parameters are adjusted. Exemplary adjustments include: removal of an existing parameter, replacement of an existing parameter with a new parameter, adjustment of the value of an existing parameter, and addition of a new parameter. The adjustments may denote instructions to the user. For example, the amount of alcohol the user currently drinks may be adjusted to remove alcohol from the user's diet. In another example, for a user that does not exercise, an exercise regimen may be selected. In yet another example, for a user with high HbA1c values, a target HbA1c value below a threshold may be set. The adjustment may be performed in response to a received indication signal, which is generated in response to manual user input (e.g., user changes to one or more parameters, for example, by making a new selection using a parameter selection user interface (e.g., GUI), and/or in response to automatic input generated by executing code (e.g., process that automatically tries different parameters and/or values of parameters according to a set of rules to obtain a target aggregated risk level below a threshold).

Optionally, one or more patient-specific medications and/or one or more patient-specific parameters that most significantly contribute to the aggregated risk score(s) for one or more predicted medical outcomes are identified. The patient-specific medications and/or patient-specific parameters that result in the aggregated risk score(s) for the predicted medical outcome(s) to be above the risk threshold may be identified. The identified patient-specific medication(s) and/or patient-specific parameter(s) may be adjusted to reduce the aggregated scores for the predicted medical outcome(s) below the risk threshold. The patient-specific medications and/or patient-specific parameters may be identified, for example, by analyzing for each respective predicted medical outcome, the identified relationship-mappings including the respective predicted medical outcome, to determine at least one medication and/or at least one patient parameter contributing statistically significantly and disproportionally to the computed aggregated risk score relative to other medications and/or other patient parameters. The determined medication and/or patient parameter may be identified as a significant risk factor for the patient for developing the respective medical outcome. An adjustment to the identified medication(s) and/or patient parameter(s) may be received (manually and/or automatically), for reducing risk of the respective medical outcome to below the risk threshold. The patient may be treated using the selected adjustment.

At 116, instructions are generating for creating dynamic drug labels. Optionally, a respective dynamic drug label is created for each one of the patient-specific medications.

Each dynamic drug label may include one or more sub-aggregated risk scores. Each sub-aggregated risk score may be computed for each respective predicted medical outcome (for the respective patient-specific medication) by aggregating the risk scores of the identified relationship-mappings including the respective predicted medical outcome and the respective patient-specific medication. For example, the identified relationship-mappings are first clustered according to respective unique patient-specific medication, and then, each cluster is further sub-clustered according to unique respective predicted medical outcomes. The sub-aggregated risk score is computed per predicted medical outcome (for each patient-specific medication, e.g., per cluster), by aggregating the risk scores of the relationship-mappings of each predicted medical outcome (e.g., per sub-cluster).

The dynamic drug labels may be provided, for example, printed on a sticker at the pharmacy for sticking on the package of each respective drug, printed on paper at the pharmacy, provided as digital data to the patient (e.g., sent to an email of the patient, sent to a mobile device of the patient), and/or provided as a link to access the dynamic drug labels stored on a server.

The dynamic labels may be dynamically updated based on an update of the mapping data-structure, for example, iterating features 102 and 114. For example, the dynamic labels may be periodically updated using current data of the mapping data-structure (e.g., every defined period of time, such as once a month), and/or the update may be triggered by an update to the mapping-dataset. The digital and/or paper based updated dynamic labels may be provided to the user.

The dynamic drug label may be created in response to the adjustment as in 114. For example, when the user has performed one or more adjustments until a final set of patient-specific medications are selected, the dynamic drug label may be created based on the final set. Alternatively or additionally, the dynamic drug label may be created during each iteration cycle of 102 (or 104) to 112.

At 118, one or more aggregated risk scores computed for the patient are monitored. The monitoring may be performed by iterating one or more features described with reference to 102-114, periodically, for example, once every predefined time interval, such a once every day, week, once, quarter, 6 months, year, or other time interval.

Optionally, a trend for the aggregated risk scores obtained over multiple time intervals is computed, for example, a linear trend line is fitted using a least mean square approach. The trend may be used to predict whether the aggregated risk scores will cross a threshold in the future. An alert may be generated, for example, sent to a mobile device of a user, sent as an email, and/or a pop-up is generated on a display. An adjustment may be made (e.g., as described herein) to the patient-specific medications and/or patient-specific parameters in an effort to prevent the aggregated risk scores from cross the threshold in the future.

Monitoring may be performed per patient, for example, as a form of customized supervision of each patient over time.

At 120, a training dataset for training a machine learning model is generated.

The training dataset may be generated by iterating one or more of 102 (or 104) to 118 (e.g., 104-112) for each one or multiple sample patients, each having a respective set of patient-specific medications and patient-specific parameters, to generate a corresponding set of aggregated risk score for each respective predicted medical outcome for each of the sample patients. An input (e.g., vector) of the training dataset is created by designating the set of patient-specific medications and patient-specific parameters as input. An output (e.g., vector) of the training dataset, denoting a label, is created by designating the corresponding aggregated risk score for predicted medical outcome for each of the sample patients as input.

The labelling of the training dataset as described herein may replace and/or augment a hand-labelled (or other manual) process for generating the training dataset.

The training dataset is provided for training the machine learning model.

The machine learning model may be trained using the training dataset.

The machine learning model may be trained using a supervised learning approach using the labels of the input data. The machine learning model is trained for prediction of an aggregated risk score for each respective predicted medical outcome of a target patient in response to being fed the patient-specific medications and the patient-specific parameters of the target patient.

The machine learning model may be trained using a weak supervision approach. The weak supervision approach may not necessarily provide 100% accuracy in ground truth. For example, that a stroke in a patient is predicted to be cause by (or has occurred due to) certain medications. The labelling described herein and/or weak supervision approach described herein assigns higher weights to identified associations, and relatively lower weights where no clear associations are identified. The labelling described herein and/or weak supervision approach described herein improves the ability of the trained machine learning model to overcome noise in the data and to learn.

The machine learning model may, for example, enable outputting aggregated risk scores when certain relationship-mappings are not found in the mapping data-structure.

Exemplary machine learning models include one or more neural networks of various architectures (e.g., artificial, deep, convolutional, fully connected), Markov chains, support vector machine (SVM), logistic regression, k-nearest neighbor, and decision trees.

At 122, the patient is treated in view of the aggregated risk score computed for each unique predicted medical outcome. Instructions may be generated for treating the patient in view of the aggregated risk score computed for each unique predicted medical outcome. For example, a prescription for the patient is generated according to the selected patient medications. In another example, text, video, and/or audio recommendations are generated for the patient to comply with selected patient-parameters, such as the adjusted parameters that are predicted to result in aggregated risk scores of predicted medical outcomes below the target risk threshold. For example, the patient is provided with instructions to stop smoking, reduce alcohol consumption, exercise using a provided exercise regimen, and/or a diet is generated for the patient to obtain a target nutrition (e.g., to reduce cholesterol levels below a target).

The patient may be treated based on the instructions. For example, the patient takes the prescribed medication and/or follows the instructions, such as to change diet, stop smoking, exercise, and/or reduce alcohol consumption.

Optionally, the patient may be treated using the initially planned prescription after the user (e.g., physician, pharmacist) views the aggregated risk scores, and determines that the risk is acceptable in view of the benefits to the patient by taking the drugs. Alternatively, the patient may be treated using a different set of prescribed medications, that were selected based on the aggregated risk scores computed for the initially planned prescriptions, as described with reference to 114.

Referring now back to FIG. 3, at 302, raw medical data is obtained.

The raw medical data is extracted, for example, from one or more of: formal prescribing information (e.g., from the FDA), pharmaceutical leaflets, drug information databases, medical database, medical literature, clinical trials, and adverse drug reaction reports.

The raw medical data may be extracted, for example, using natural language processing (NLP) that searches for key words related to pharmacodynamics, pharmacokinetics, drugs, patient-parameters, and/or predicted medical outcomes.

The raw medical data may be obtained, for example, by crawling code that crawls along a network (e.g., internet) between websites hosting medical data, by receiving new published medical data as a subscription to a service (e.g., emails and/or feeds of the new data), accessing a set of servers hosting medical data.

Data may be inserted manually, semi-automatically, and/or automatically, for example, via APIs.

At 304, multiple features are extracted from the raw medical data. Each feature corresponds to one or more of: medication(s), predicted medical outcome(s), patient parameter(s), and value(s) for computing a corresponding risk value.

Extracted features may include active ingredients of medications. It is noted that a certain active ingredient may map to multiple medications.

Extracted features may include pharmacokinetics and/or pharmacodynamics of the medications and/or for the sub-components (i.e., active ingredients) of the medications, for example, blood level, absorption, distribution, metabolism, and elimination.

Exemplary extracted features include: a medication influencing factor directly affecting a corresponding mapped medication which affects a medication induced event, and an event influencing factor directly affecting the medication induced event. Exemplary medication influencing factors include primary parameters affecting the corresponding mapped medication, for example: blood level, absorption, distribution, metabolism, elimination. Exemplary medication influencing factors include secondary parameters affecting the primary parameter, for example: other medication, medication condition, and non-genetic parameters of the patient that are unrelated to known genetic sequences.

At 306, relationship-mapping(s) are determined between the extracted features. Each relationship-mapping maps between a certain medication, a certain medical outcome, and a certain patient parameter, with a certain individual risk score, as described herein.

The relationship-mappings may be defined, for example, based on a set of rules, trained machine learning model, and/or based on a domain model generated based on domain expertise of a user.

It is noted that the determined relationship-mappings may represent new identified relationships between drug parameters, patient parameters, and predicted medical outcomes, which may not necessarily be known in the medical literature.

At 308, the determined relationship-mapping(s) are stored in the mapping data-structure.

At 310, one or more of 302-308 are iterated for dynamically updating the mapping data-structure with new relationship-mappings, for example, upon predefined time intervals (e.g., every hour, day, week, or other time interval), continuously (e.g., code that continuously crawls the internet to find new data), and/or when triggered (e.g., when new data is received).

Various embodiments and aspects of the present invention as delineated hereinabove and as claimed in the claims section below find experimental and/or calculated support in the following examples.

EXAMPLES

Reference is now made to the following examples, which together with the above descriptions illustrate some embodiments of the invention in a non-limiting fashion.

Inventors obtained medical data for 30 real patients. The medications, medical conditions, and lab results were processed as described herein. An aggregated risk score was computed for multiple predicted medical outcomes. Medication for the same patients was fed into an existing system, which outputs a set of ADR alerts. A physician was consulted and asked regarding these patients. The physician advised regarding foreseen problems, and which patients are at risk for the problems. The physician's input was cross reference with the outputs of an application generated according to the systems, methods, apparatus, and/or code instructions described herein, and with the existing system. Inventors found that the existing system generated over 75% false alerts and had about 33% accuracy in average across all patients. In contrast, the application generated according to the systems, methods, apparatus, and/or code instructions described herein generated less than 10% false alerts and a 73% accuracy across all patients in identification and prediction of ADRs based on the data input.

The experimental and/or calculated results show that the systems, methods, apparatus, and/or code instructions described improve the technology of predicting medical outcomes in patients treated with multiple medications, and/or improve the computer computing the predicted medical outcomes, by reducing false alerts and/or increasing accuracy, in comparison to existing approaches.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant medications will be developed and the scope of the term medication is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method of training a machine learning model for assessing risk of at least one predicted medical outcome for a patient having a plurality of patient-specific parameters and future planned treatment with a plurality of patient-specific medications, comprising:
   in a pre-processing step, for each of a plurality of sample patients:
      mapping a plurality of patient-specific medications and a plurality of patient-specific parameters to a plurality of risk scores of a plurality of medical outcomes by a mapping data structure that includes a plurality of relationship-mappings that map between a plurality of medications, a plurality of predicted medical outcomes, and a plurality of patient parameters, wherein each relationship-mapping includes at least one respective medication of the plurality of medications, at least one respective predicted medical outcome of the plurality of medical outcomes, at least one respective patient parameter of the plurality of patient parameters, and at least one respective risk score for the at least one respective predicted medical outcome,
      wherein at least one of the plurality of relationship-mappings includes a predicted medical outcome denoting a medication induced event of a medication of the plurality of medications, and at least one patient parameter selected from the group consisting of: a medication influencing factor directly affecting the medication which affects the medication induced event, and an event influencing factor directly affecting the medication induced event,
      wherein the medication influencing factor is selected from the group consisting of the following primary parameters affecting the medication: blood level, absorption, distribution, metabolism, elimination, half life elimination, and pharmacodynamics,
      wherein at least one patient-specific medication is mapped to a plurality of active ingredients, and wherein a subset of the plurality of relationship-mappings each include a respective active ingredient of the plurality of active ingredients, and the medication influencing factor is for the respective active ingredient;
      computing an aggregated risk score for each respective predicted medical outcome by aggregating the risk scores of the plurality of relationship-mappings including each respective predicted medical outcome identified by the mapping data-structure; and
      automatically designating the aggregated risk score as a ground truth label for a record corresponding to the sample patient for creating a training dataset for training a machine learning model;
   in a training step, creating the training dataset comprising a plurality of records for a plurality of sample patients, wherein a record of a sample patient is computed by:
      defining an input vector as a respective plurality of patient-specific medications and a respective plurality of patient-specific parameters of the sample patient mapped by the mapping data-structure, and
      designating an output vector as the ground truth label, the output vector including the aggregated risk score computed for each respective predicted medical outcome; and
   training a machine learning model on the training dataset using a supervised learning approach using the ground truth label, by iteratively teaching the machine learning model to infer a function that maps the input vector of each record of the training dataset to the corresponding ground truth label of the record,
   wherein the machine learning model is iteratively trained to learn the function that predicts a target aggregated risk score for each respective target predicted medical outcome in response to being fed a plurality of target patient-specific medications and a plurality of target patient-specific parameters for a target patient,
   wherein the machine learning model generates the predicted target aggregated risk score without accessing the mapping data-structure.

2. The method of claim 1, wherein the medication influencing factor is selected from the group consisting of the following secondary parameters affecting the primary parameter: other medication, medication condition, and non-genetic parameters of the patient that are unrelated to known genetic sequences.

3. The method of claim 1, wherein each aggregated risk score denotes a personalized predicted risk assessment of the patient being treated with the plurality of patient-specific medications and having the patient-specific parameters developing the respective predicted medical outcome, and each respective risk score of each respective relationship-mapping is indicative of a probability of a certain patient being treated with the one respective medication and having the one respective patient parameter, developing the one respective predicted medical outcome.

4. The method of claim 1, wherein the identified plurality of relationship-mappings are clustered according to respective predicted medical outcomes, wherein relationship-mapping members of each cluster have a common predicted medical outcome, and wherein the computing the aggregated risk score comprises aggregating the risk scores of the relationship-mapping members of each respective cluster.

5. The method of claim 1, wherein at least one of the plurality of patient-specific parameters comprises an influence of a certain patient-specific medication on another certain patient-specific medication, and the predicted medical outcome is a result of the influence.

6. The method of claim 1, wherein the aggregated risk score for each respective predicted medical outcome is computed by multiplication of individual risk scores of the identified plurality of relationship-mapping including the respective predicted medical outcome.

7. The method of claim 1, wherein the aggregated risk score denotes a positive increase or a negative decrease relative to a baseline risk score of the respective predicted medication outcome.

8. The method of claim 1, further comprising receiving an indication signal denoting an adjusted at least one of the plurality of patient-specific medications created by an adjustment of the at least one of the plurality of patient-specific medications, wherein the adjustment is selected from the group consisting of: removal, replacement, adjustment of dose, and addition, and iteratively feeding the adjusted at least one of the plurality of patient-specific medications into the trained machine learning model, for obtaining respective predicted target aggregated risk scores.

9. The method of claim 8, wherein the adjustment is iterated until the aggregated risk score for each respective predicted medical outcome is less than a risk threshold, and instructions are generated for treating the patient to prevent or reduce risk of each respective predicted medical outcome below the risk threshold.

10. The method of claim 1, further comprising receiving an indication signal denoting an adjustment of at least one of the plurality of patient-specific parameters, wherein the adjustment is selected from the group consisting of: removal, replacement, adjustment of value, and addition, and iterating using the adjustment of the at least one of the plurality of patient-specific parameters, the identifying the plurality of relationship-mappings, the computing the aggregated risk factor, and instructions are generated for treatment of the patient using the adjustment.

11. The method of claim 10, wherein the adjustment is iterated until the aggregated risk score for each respective predicted medical outcome is less than a risk threshold, and the instructions are generated for treating the patient to prevent or reduce risk of each respective predicted medical outcome below the risk threshold.

12. The method of claim 1, further comprising creating and/or updating the mapping data-structure, by:
obtaining raw medical data;
extracting a plurality of features from the raw medical data corresponding to at least one medication, at least one predicted medical outcome, at least one patient parameter, and values for computing a corresponding risk value;
computing at least one relationship-mapping between the extracted features; and
storing the at least one relationship-mapping in the mapping data-structure.

13. The method of claim 12, wherein the raw medical data is extracted using natural language processing (NLP) from one or more members of the group consisting of: formal prescribing information, pharmaceutical leaflets, drug information databases, medical database, medical literature, clinical trials, adverse drug reaction reports.

14. The method of claim 1, wherein computing the aggregated risk score comprises determining a risk classification category of a plurality of risk classification categories each indicative of a range of values of risk scores.

15. The method of claim 14, further comprising generating instructions for presenting a table of risk classification categories, and placing each respective predicted medical outcome into one of the risk classification categories of the table according to the respective determined risk classification category.

16. The method of claim 15, wherein each predicted medical outcome stored in the mapping data-structure is associated with a certain severity category selected from a plurality of severity categories, and the presented table includes a plurality of cells each denoting a respective risk classification category and a respective severity category, wherein each respective predicted medical outcome is placed into one of the plurality of cells based on the corresponding aggregated risk score and corresponding certain severity category.

17. The method of claim 16, wherein when at least one of the plurality of patient-specific parameters matches at least one predicted medical outcome, creating a set of cells in the table denoting current medical outcomes, and placing each of the plurality of patient-specific parameters into one of the cells according to respective severity category of the respective current medical outcome.

18. The method of claim 1, wherein the plurality of patient-specific parameters are non-genetic parameters that are unrelated to known genetic sequences.

19. The method of claim 18, wherein the non-genetic patient-specific parameters of the patient are selected from the group consisting of: smoking, alcohol, nutrition, amount of exercise, occupation, lifestyle data, past usage of medications, current usage of medications, current medical conditions, past medical condition, past medical treatments, current diagnosis, symptoms, lab test results, and imaging results.

20. The method of claim 1, further comprising, analyzing for each respective predicted medical outcome, the identified plurality of relationship-mappings including the respective predicted medical outcome to determine at least one medication and/or at least one patient parameter contributing statistically significantly and disproportionally to the computed aggregated risk score relative to other medications and/or other patient parameters, and providing the determined at least one medication and/or at least one patient parameter as a significant risk factor for the patient for developing the respective medical outcome, and further comprising selecting an adjustment for the at least one medication and/or at least one patient parameter for reducing risk of the respective medical outcome to below a risk threshold, and instructions are generated for treatment of the patient based on the selected adjustment.

21. The method of claim 1, further comprising generating instructions for generating a plurality of dynamic drug labels, each dynamic drug label computed for each one of the plurality of patient-specific medications, each dynamic drug label including a plurality of sub-aggregated risk scores, each sub-aggregated risk score computed for each respective predicted medical outcome of the respective patient-specific medication by aggregating the risk scores of the identified plurality of relationship-mappings including the respective predicted medical outcome and the respective patient-specific medication.

22. The method of claim 21, further comprising dynamically updating each one of the plurality of dynamic labels based on an update of the mapping data-structure.

23. The method of claim 1, wherein at least one of the plurality of predicted medical outcomes denote an efficacy of treating a target disease, and the aggregated risk score for the at least one of the plurality of predicted medical outcomes comprises a change in efficacy relative to a baseline efficacy.

24. The method of claim 1, further comprising monitoring aggregated risk scores for the predicted medical outcomes, by: computing a plurality of aggregated risk scores for each respective predicted medical outcomes over a plurality of time intervals, computing a trend according to the plurality of aggregated risk scores, and analyzing the trend to generate an alert when at least one of the aggregated risk scores is predicted to cross a threshold.

25. A system for training a machine learning model for assessing risk of at least one predicted medical outcome for a patient having a plurality of patient-specific parameters and future planned treatment with a plurality of patient-specific medications, comprising:
at least one hardware processor executing a code for:
in a pre-processing step, for each of a plurality of sample patients:
mapping a plurality of patient-specific medications and a plurality of patient-specific parameters to a plurality of risk scores of a plurality of medical outcomes by a mapping data structure that includes a plurality of relationship-mappings that map between a plurality of medications, a plurality of predicted medical outcomes, and a plurality of patient parameters, wherein each relationship-mapping includes at least one respective medication of the plurality of medications, at least one respective predicted medical outcome of the plurality of medical outcomes, at least one respective patient parameter of the plurality of patient parameters, and at least one respective risk score for the one respective predicted medical outcome,
wherein at least one of the plurality of relationship-mappings includes a predicted medical outcome denoting a medication induced event of a medication of the plurality of medications, and at least one patient parameter selected from the group consisting of: a medication influencing factor directly affecting the medication which affects the medication induced event, and an event influencing factor directly affecting the medication induced event,
wherein the medication influencing factor is selected from the group consisting of the following primary parameters affecting the medication: blood level, absorption, distribution, metabolism, elimination, half life elimination, and pharmacodynamics,
wherein at least one patient-specific medication is mapped to a plurality of active ingredients, and wherein a subset of the plurality of relationship-mappings each include a respective active ingredient of the plurality of active ingredients, and the medication influencing factor is for the respective active ingredient;
computing an aggregated risk score for each respective predicted medical outcome by aggregating the risk scores of the plurality of relationship-mappings including each respective predicted medical outcome identified by the mapping data-structure; and
automatically designating the aggregated risk score as a ground truth label for a record corresponding to the sample patient for creating a training dataset for training a machine learning model;
in a training step, creating the training dataset comprising a plurality of records for a plurality of sample patients, wherein a record of a sample patient is computed by:
defining an input vector as a respective plurality of patient-specific medications and a respective plurality of patient-specific parameters of the sample patient mapped by the mapping data-structure, and designating an output vector as the ground truth label, the output vector including the aggregated risk score computed for each respective predicted medical outcome; and
training a machine learning model on the training dataset using a supervised learning approach using the ground truth label, by iteratively teaching the machine learning model to infer a function that maps the input vector of each record of the training dataset to the corresponding ground truth label of the record,
wherein the machine learning model is iteratively trained to learn the function that predicts a target aggregated risk score for each respective target predicted medical outcome in response to being fed a plurality of target patient-specific medications and a plurality of target patient-specific parameters for a target patient,
wherein the machine learning model generates the predicted target aggregated risk score without accessing the mapping data-structure.

26. A method of assessing risk of at least one predicted medical outcome for a patient having a plurality of patient-specific parameters and future planned treatment with a plurality of patient-specific medications, comprising:
feeding a plurality of target patient-specific medications and a plurality of target patient-specific parameters for a target patient into a machine learning model; and
obtaining an outcome of a predicted target aggregated risk score for each one of a plurality of target predicted medical outcomes,
wherein the machine learning model generates the predicted target aggregated risk score without accessing the mapping data-structure,
wherein the machine learning model is trained on a training dataset using a supervised learning approach using ground truth labels, by iteratively teaching the machine learning model to iteratively infer a function that maps the input vector of each record of the training dataset to the corresponding ground truth label of the record,
wherein the training set comprises: in a pre-processing step, for each of a plurality of sample patients:
mapping a plurality of patient-specific medications and a plurality of patient-specific parameters to a plurality of risk scores of a plurality of medical outcomes by a mapping data structure that includes a plurality of relationship-mappings that map between a plurality of medications, a plurality of predicted medical outcomes, and a plurality of patient parameters, wherein each relationship-mapping includes at least one respective medication of the plurality of medications, at least one respective predicted medical outcome of the plurality of medical outcomes, at least one respective patient parameter of the plurality of patient parameters, and at least one respective risk score for the at least one respective predicted medical outcome,
wherein at least one of the plurality of relationship-mappings includes a predicted medical outcome denoting a medication induced event of a medication of the plurality of medications, and at least one patient parameter selected from the group consisting of: a medication influencing factor directly affecting the medication which affects the medication induced event, and an event influencing factor directly affecting the medication induced event, wherein the medication influencing factor is selected from the group consisting of the following primary parameters affecting the medication: blood level, absorption, distribution, metabolism, elimination, half life elimination, and pharmacodynamics, wherein at least one patient-specific medication is mapped to a plurality of active ingredients, and wherein a subset of the plurality of relationship-mappings each include a respective active ingredient of the plurality of active ingredients, and the medication influencing factor is for the respective active ingredient;

computing an aggregated risk score for each respective predicted medical outcome by aggregating the risk scores of the plurality of relationship-mappings including each respective predicted medical outcome identified by the mapping data-structure;

automatically designating the aggregated risk score as a ground truth label for a record corresponding to the sample patient for creating a training dataset for training a machine learning model;

in a training step, creating the training dataset comprising a plurality of records for a plurality of sample patients, wherein a record of a sample patient is computed by:

defining an input vector as a respective plurality of patient-specific medications and a respective plurality of patient-specific parameters of the sample patient mapped by the mapping data-structure, and designating an output vector as the ground truth label, the output vector including the aggregated risk score computed for each respective predicted medical outcome.

27. The method of claim 1, wherein the machine learning model is trained using a weak supervision approach.

28. The method of claim 1, further comprising treating the patient in view of the aggregated risk score for each unique predicted medical outcome.

29. The method of claim 1, wherein the mapping data-structure is implemented as a member selected from a group consisting of: a table, and a set of pointers, and wherein the machine learning model is implemented as a member selected from a group consisting of: neural network, Markov chains, support vector machine (SVM), logistic regression, k-nearest neighbor, and decision trees.

* * * * *